(12) United States Patent
Shiozawa

(10) Patent No.: US 6,623,924 B1
(45) Date of Patent: Sep. 23, 2003

(54) METHOD FOR DETERMINING SUSCEPTIBILITY TO RHEUMATOID ARTHRITIS

(76) Inventor: Shunichi Shiozawa, 11-6 Takenodai 2-chome, Nishi-ku, Kobe-shi, Hyogo, 651-2274 (JP)

( * ) Notice: Subject to any disclaimer, the term of this patent is extended or adjusted under 35 U.S.C. 154(b) by 0 days.

(21) Appl. No.: 09/423,861

(22) PCT Filed: Apr. 10, 1998

(86) PCT No.: PCT/JP98/01665

§ 371 (c)(1),
(2), (4) Date: Jan. 31, 2000

(87) PCT Pub. No.: WO98/51791

PCT Pub. Date: Nov. 19, 1998

(30) Foreign Application Priority Data

May 15, 1997 (JP) ............................................. 9-125899
Feb. 13, 1998 (JP) ........................................... 10-031840

(51) Int. Cl.[7] .......................... C12Q 1/68; C12P 19/34; C07H 21/04
(52) U.S. Cl. .......................... 435/6; 435/91.1; 435/91.2; 536/23.1; 536/24.33
(58) Field of Search ............................. 536/23.1, 24.33; 435/6, 91.2, 91.1

(56) References Cited

PUBLICATIONS

Hayashi et al. "A preliminary study of the use of unaffected siblings for the marker allele frequence of sib–pari linkage analysis" Bulletin gof Allied Medical Sciences, Kobe, 1997, 13: 157–161.*

Murray et al. "A Comprehensive Human Linkage Map with Centimorgan Density" 1994, Science 265:2049–2054.*

Gomolka et al. "Immunoprinting: various genes are associated with increased risk to develop rheumatoid arthritis in different groups of adult patients" 1995, J. Mol. Med. 73:19–20.*

Tsao et al. "Evidence for linkage of a candidate chromosome 1 region to human systemic lupus erythematosus" J Clin. Invest. 1997 99(4):725–731.*

Lou et al. Affected–Sib–Pair mapping of a novel susceptibility gene to inculin–dependent diabetes mellitus on chromosome 6q25–q27, 1995, 57:911–919.*

* cited by examiner

Primary Examiner—W. Gary Jones
Assistant Examiner—B J Forman
(74) Attorney, Agent, or Firm—Darby & Darby

(57) ABSTRACT

The application provides genes causative of rheumatoid arthritis, which are located within ±1 centimorgan from DNA sequences to which the microsatellite markers D1S214, D1S253, D8S556, DXS1001, DXS1047, DXS1205, DXS1227 and/or DXS1232 are hybridized: a method for diagnosing rheumatoid arthritis, including amplifying the genomic DNA of a subject by PCR using at least one of the microsatellite markers as primer and comparing the PCR products thereof with the PCR products prepared in the same manner using the genomic DNA of a normal control; and a method for identifying the causative factors of rheumatoid arthritis including the same as described above.

1 Claim, 17 Drawing Sheets

(1 of 17 Drawing Sheet(s) Filed in Color)

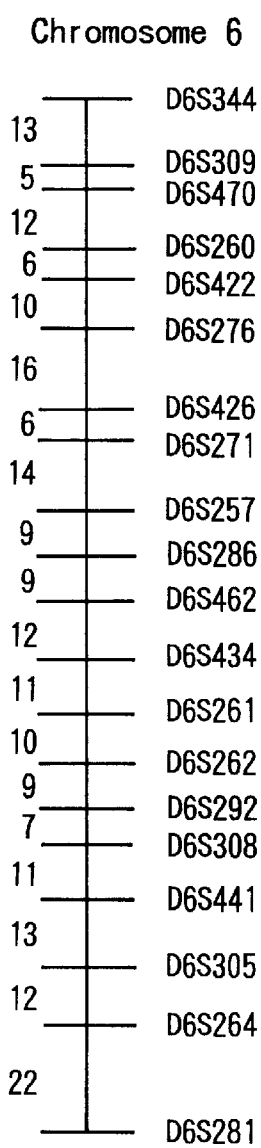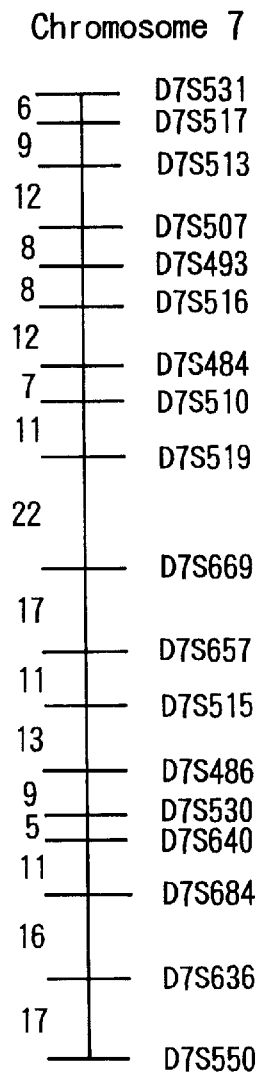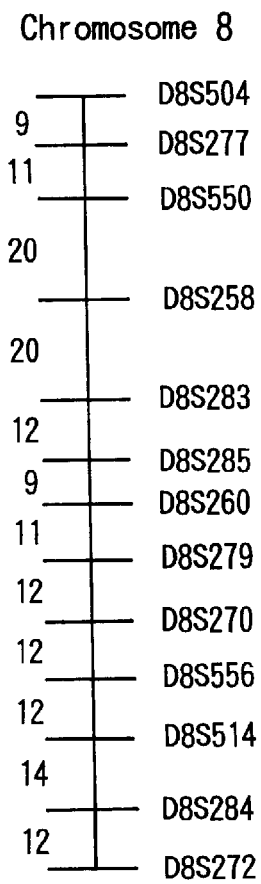
Fig. 2C
Fig. 2B
Fig. 2A

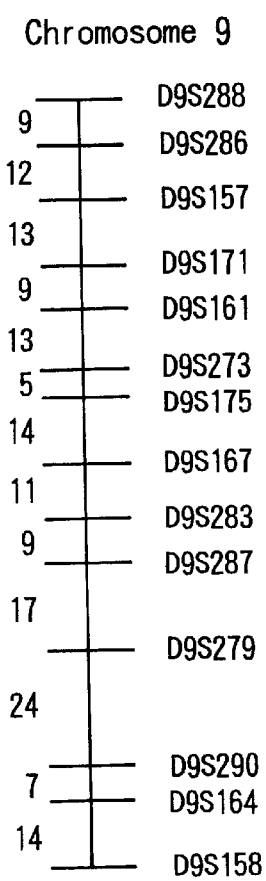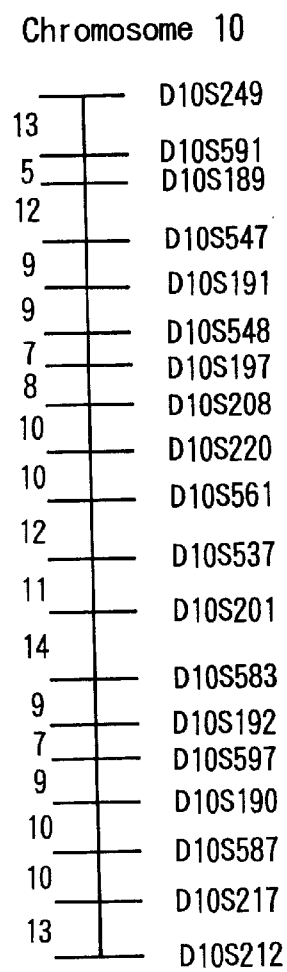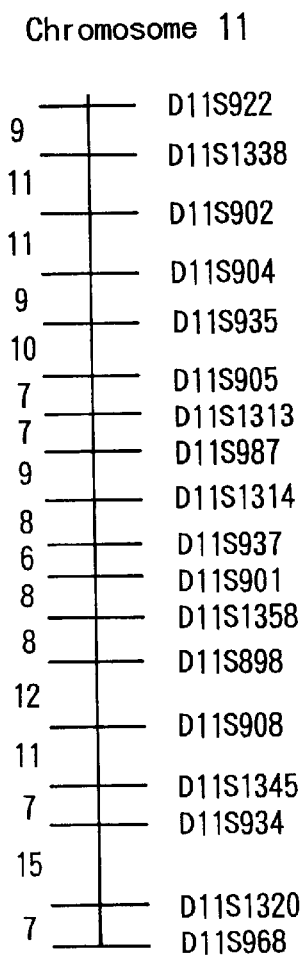
Fig. 2D
Fig. 2E
Fig. 2F

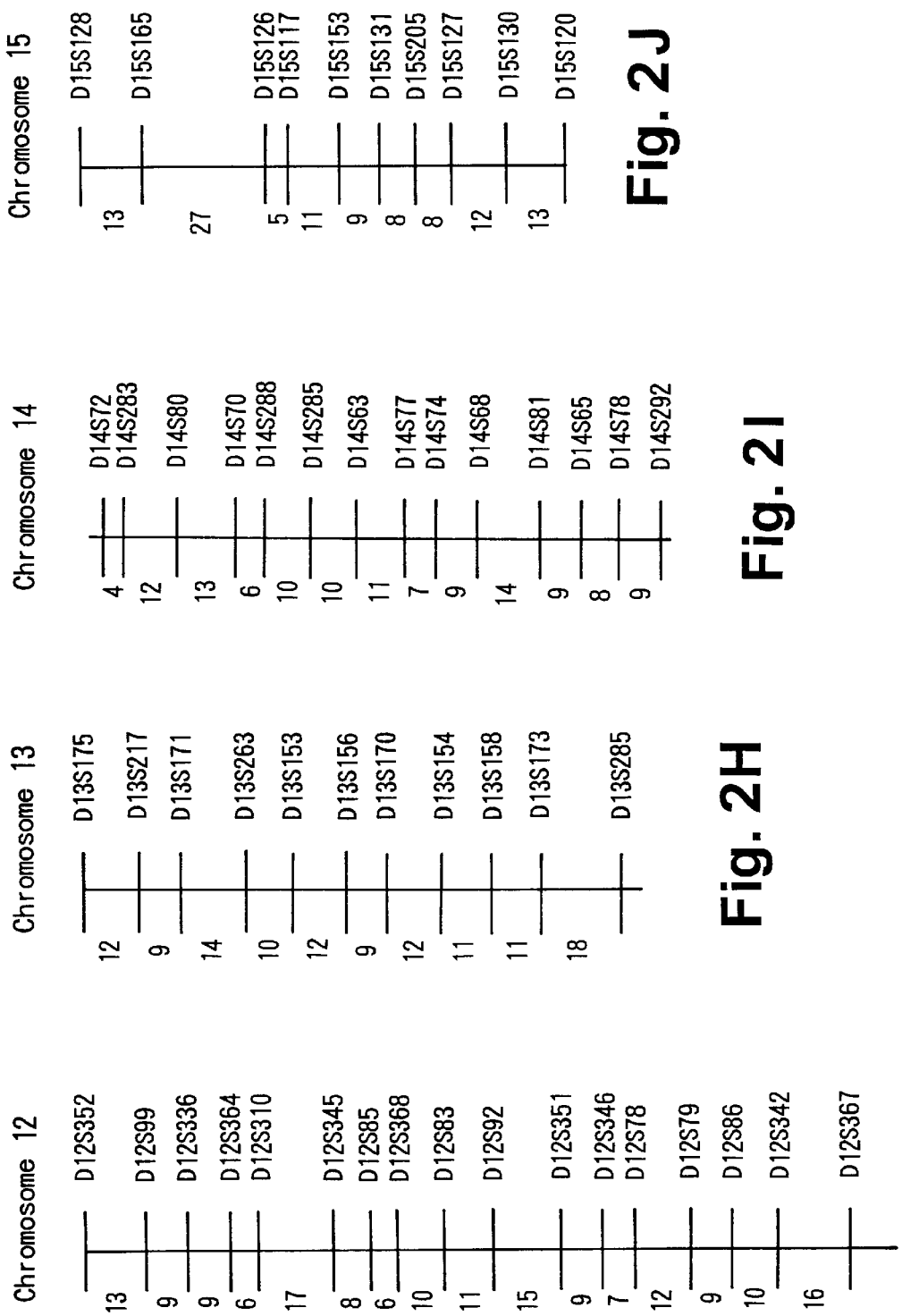

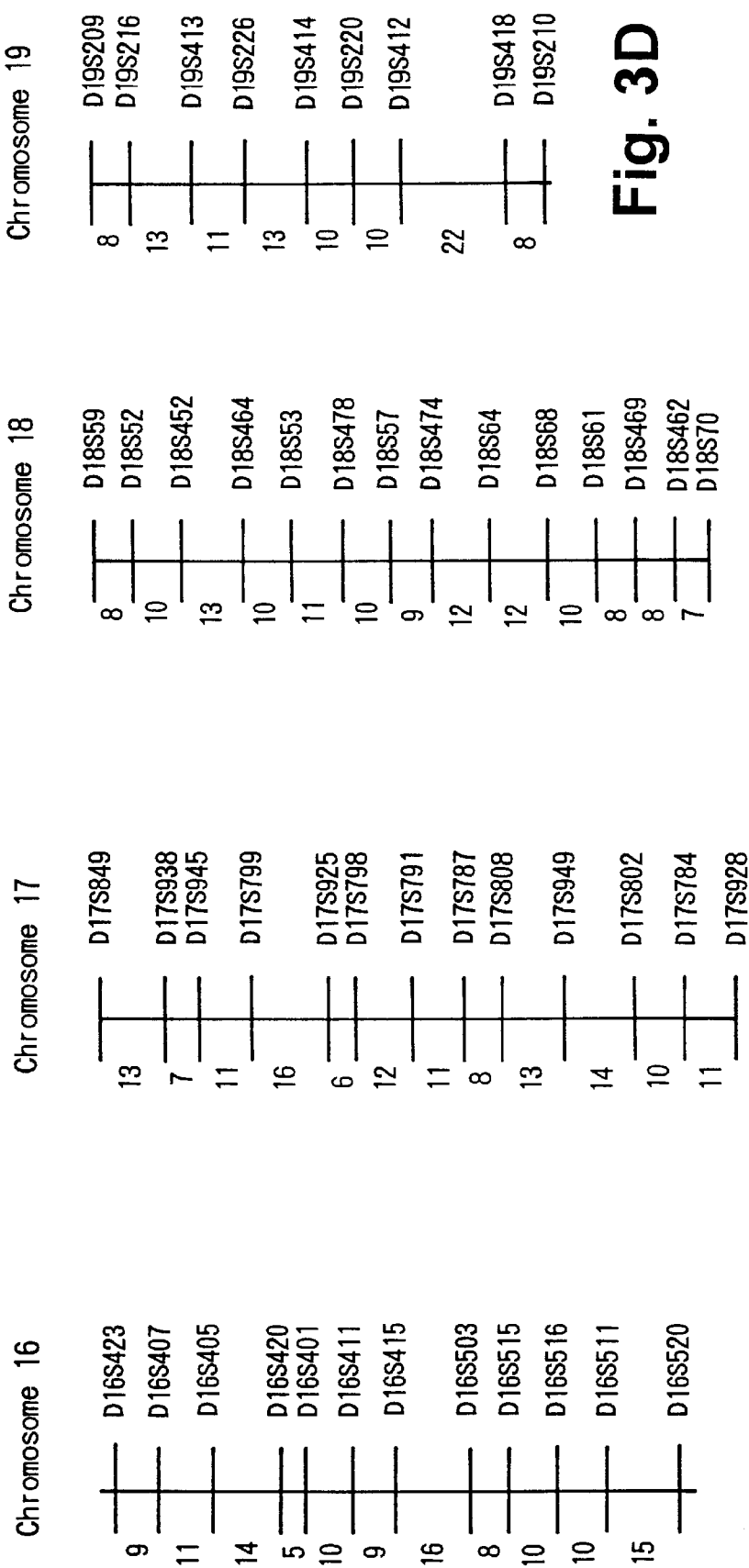

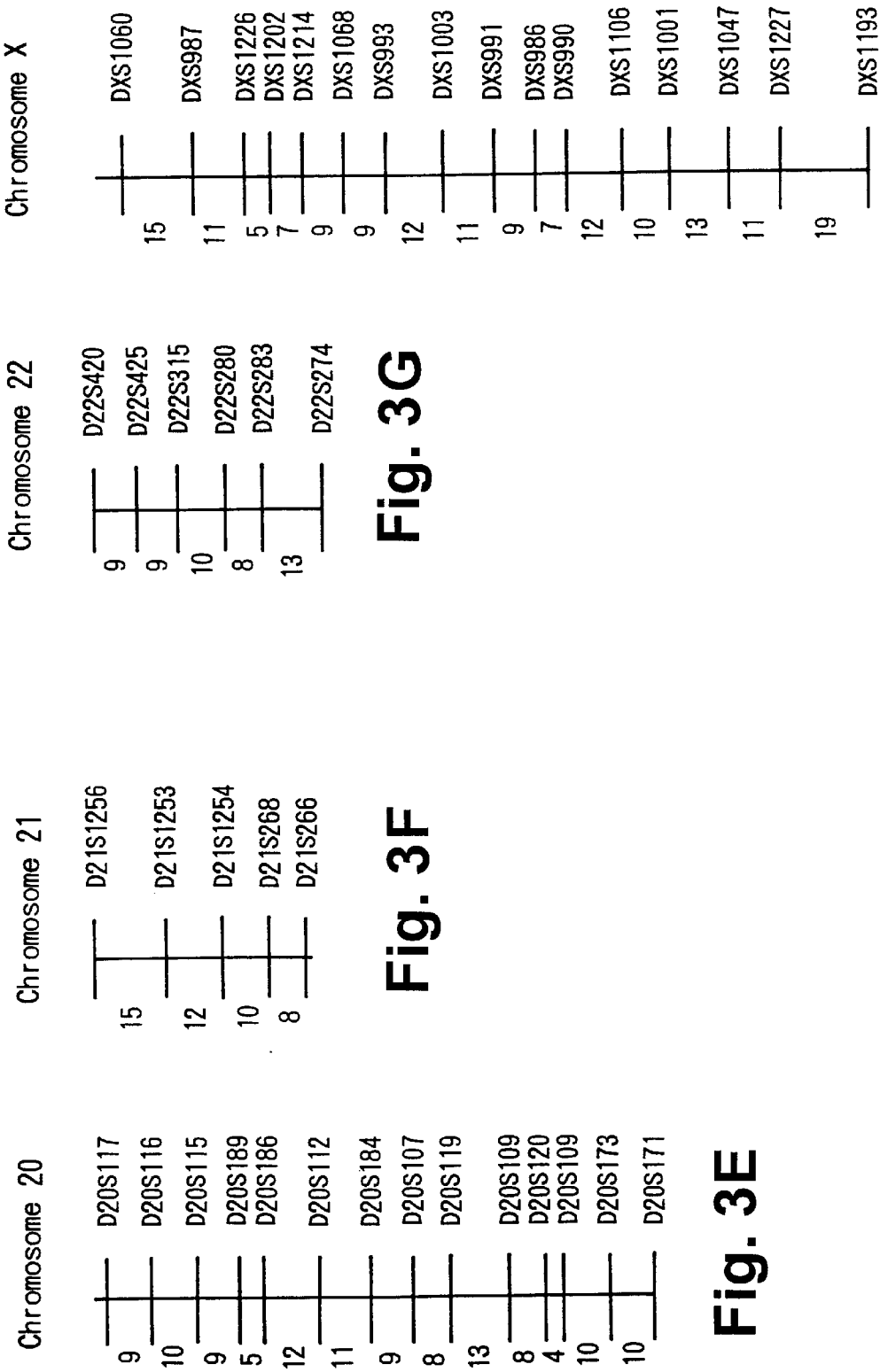

METHOD FOR DETERMINING SUSCEPTIBILITY TO RHEUMATOID ARTHRITIS

This application is a 371 of PCT/JP98/01665, filed Apr. 10, 1998.

TECHNICAL FIELD

The present invention relates to the genes causative of rheumatoid arthritis, a method for diagnosing rheumatoid arthritis using the mutations of these genes as the indicators, and a method for identifying the causative factors of rheumatoid arthritis.

BACKGROUND OF THE INVENTION

The aspects of arthritis and joint damage causing rheumatoid arthritis, particularly the pathological courses thereof, have been elucidated gradually through various research works. Because many of the autoimmune diseases including rheumatoid arthritis are induced by the concomitant participation of numerous causative factors and are then exacerbated progressively to the stage of apparent diseases, however, the interactive mechanism per se of such numerous factors should be elucidated for accurate characterization and appropriate therapeutic management of the disease.

The prevalent rheumatoid arthritis is about 1% (N. Engl. J. Med., 322: 1277–1289, 1990), but the frequency of the disease is about 8 times increased in the siblings of the patients with the disease (Cell, 85: 311–318, 1996). Hence, it is predicted that a certain genetic factor may serve as one of the causative factors. Nevertheless, molecular genetic technology and genetic engineering technology for general use for identifying the genetic factors of diseases never function effectively in case of autoimmune diseases, because the onset of autoimmune diseases is never induced via such a biologically simple mechanism as abnormal amplification of one mutated gene as in the case of cancer. Conventional strategies of traditional genetics for the elucidation of the fundamental genetic pathogenesis of diseases have demonstrated distinctively that autoimmune diseases are caused by genetic multi-factor inheritance, but the strategies were apparently insufficient. As has been described above, none of the genes involved in rheumatoid arthritis or none of the loci of the genes on chromosome have absolutely been evidenced so far.

Alternatively, the linkage analysis method and the positional cloning method by means of polymorphic markers have opened an innovative progress recently in the field of research works on genetic diseases. By using these methods, not only the chromosomal locations of disease genes previously never characterized have been identified but also the causative genes of numerous diseases have been isolated and assayed (Experimental Medicine, Vol. 12, No. 6: 80–85, 1994). More recently, the causative gene of type I diabetes mellitus has been isolated (Nature, 171: 130–136, 1994), owing to a sib-pair analysis method comprising usage of the linkage analysis using a microsatellite marker as the polymorphic marker (Nature, 359: 794–801, 1992; Nature Genet., 7: 246–336) and the analysis of patient pedigrees as one of the procedures of traditional genetics. Thus, it becomes possible that genes causing diseases hardly curable because of the current absence of any effective therapeutic means, including autoimmune diseases, will be identified.

In such circumstances and the latest progress of the research works, the present application has been submitted. It is an object of the invention to provide the genes causative of rheumatoid arthritis, the chromosomal locations of these genes firstly being specified, a method for diagnosing rheumatoid arthritis using the mutations of these genes as the indicators, and a method for identifying the causative factors of rheumatoid arthritis.

DISCLOSURE OF THE INVENTION

In accordance with the application of the invention to overcome the aforementioned problems, the following individual genes are provided.

1. A gene causative of rheumatoid arthritis, which gene is located within ±1 centimorgan from a DNA sequence on human chromosome 1 to which the microsatellite markers D1S214 and/or D1S253 are hybridized.

2. A gene causative of rheumatoid arthritis, which gene is located within ±1 centimorgan from a DNA sequence on human chromosome 8 to which the microsatellite marker D8S556 is hybridized.

3. A gene causative of rheumatoid arthritis, which gene is located within ±1 centimorgan from a DNA sequence on human chromosome X to which the microsatellite markers DXS1001, DXS1047, DXS1205, DXS1227 and/or DXS1232 are hybridized.

In accordance with the application, a method for diagnosing rheumatoid arthritis, comprising amplifying the genomic DNA of a subject by PCR method using as primer at least one of microsatellite markers D1S214, D1S253, D8S556, DXS1001, DXS1047, DXS1205, DXS1227 and DXS1232, and then comparing the resulting PCR products with the PCR products prepared in the same manner using the genomic DNA of a normal control.

In accordance with the application, furthermore, a method for identifying the causative factors of rheumatoid arthritis, comprising amplifying the genomic DNA of a subject by PCR using as primer at least one of microsatellite markers D1S214, D1S253, D8S556, DXS1001, DXS1047, DXS1205, DXS1227 and DXS1232, and then comparing the resulting PCR products with the PCR products prepared in the same manner using the genomic DNA of a normal control.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 2 is a map of microsatellite markers for use in identifying the loci of the inventive genes on the chromosomes 6 to 15;

FIG. 3 is a map of microsatellite markers for use in identifying the loci of the inventive genes on the chromosomes 16 to 22, and chromosome X;

BEST MODE FOR CARRYING OUT THE INVENTION

The method for identifying the genes of the present invention is now described in detail hereinafter.

The genes of the invention comprise plural genes having been identified of the chromosomal loci by the linkage analysis of patients with rheumatoid arthritis and their families with blood relationship. More specifically, the inventors have determined the loci of all the genes with relation to the disease sensitivity to rheumatoid arthritis, by using the DNA polymorphism (polymorphism of the length of CA repeat sequence) of microsatellite marker genes over the entire lengths of human chromosomes. The method is specifically described below.

1. Extraction of genomic DNA

A set of Patient A and another Patient B, both with rheumatoid arthritis at the stage II or higher of joint damage satisfying the clinical standard of American Rheumatism Association, and a normal sibling member C was first prepared; and then, such 35 families were analyzed as subjects. From the individuals blood was drawn peripheral blood (10 ml), using EDTA; the blood was then gradually mixed with 20 ml buffer I [0.32 M sucrose, 5% v/v Triton X-100, 5 mM $MgCl_2$, 12 mM Tris HCl (pH 7.6)], to solubilize the cell membrane. After centrifugation, precipitated nuclei reacted with buffer II [4 M guanidine thiocyanate, 12 mM EDTA, 375 mM NaCl, 0.5% sodium N-lauroyl sarcosinate, 0.1 M β-mercaptoethanol, 12 mM Tris HCl (pH 7.6)] to solubilize the nuclear membrane to extract DNA by ethanol precipitation.

2. PCR amplification and sizing of microsatellite DNA

Figure 1A:
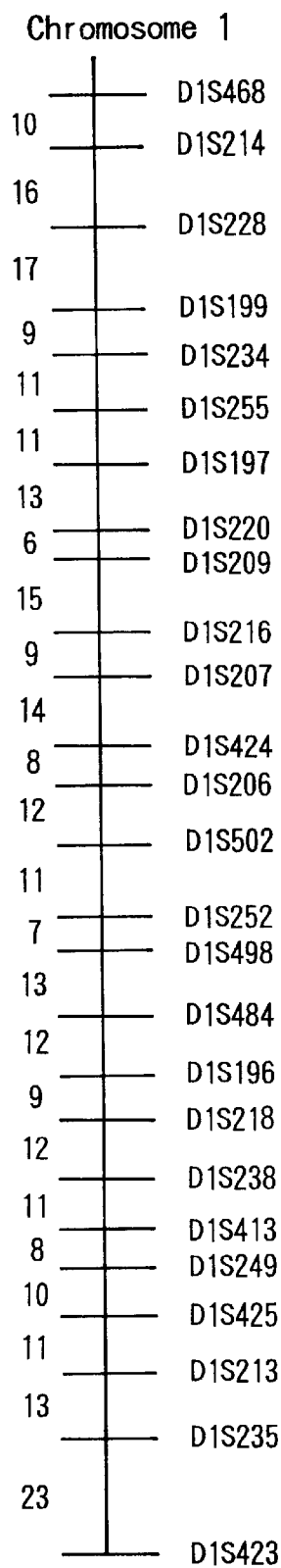
FIG. 1 is a map of microsatellite markers for use in identifying the loci of the inventive genes on the chromosomes 1 to 5.
Figure 1B:
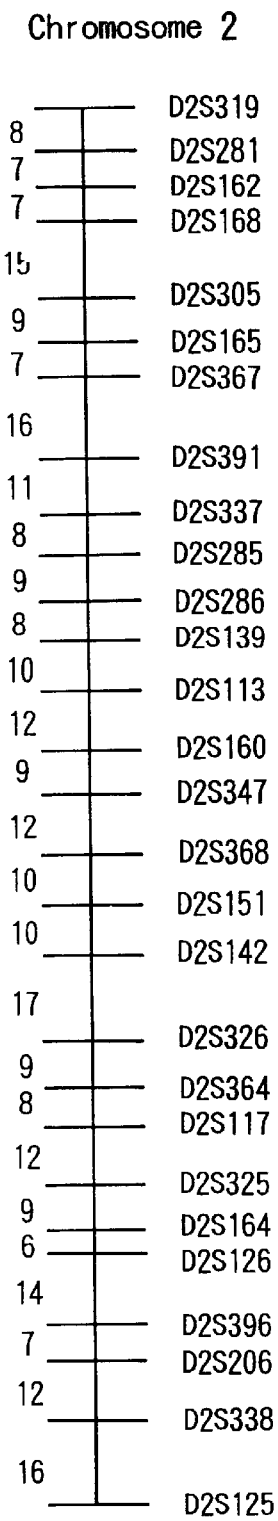
Figures 1C, 1D, 1E:
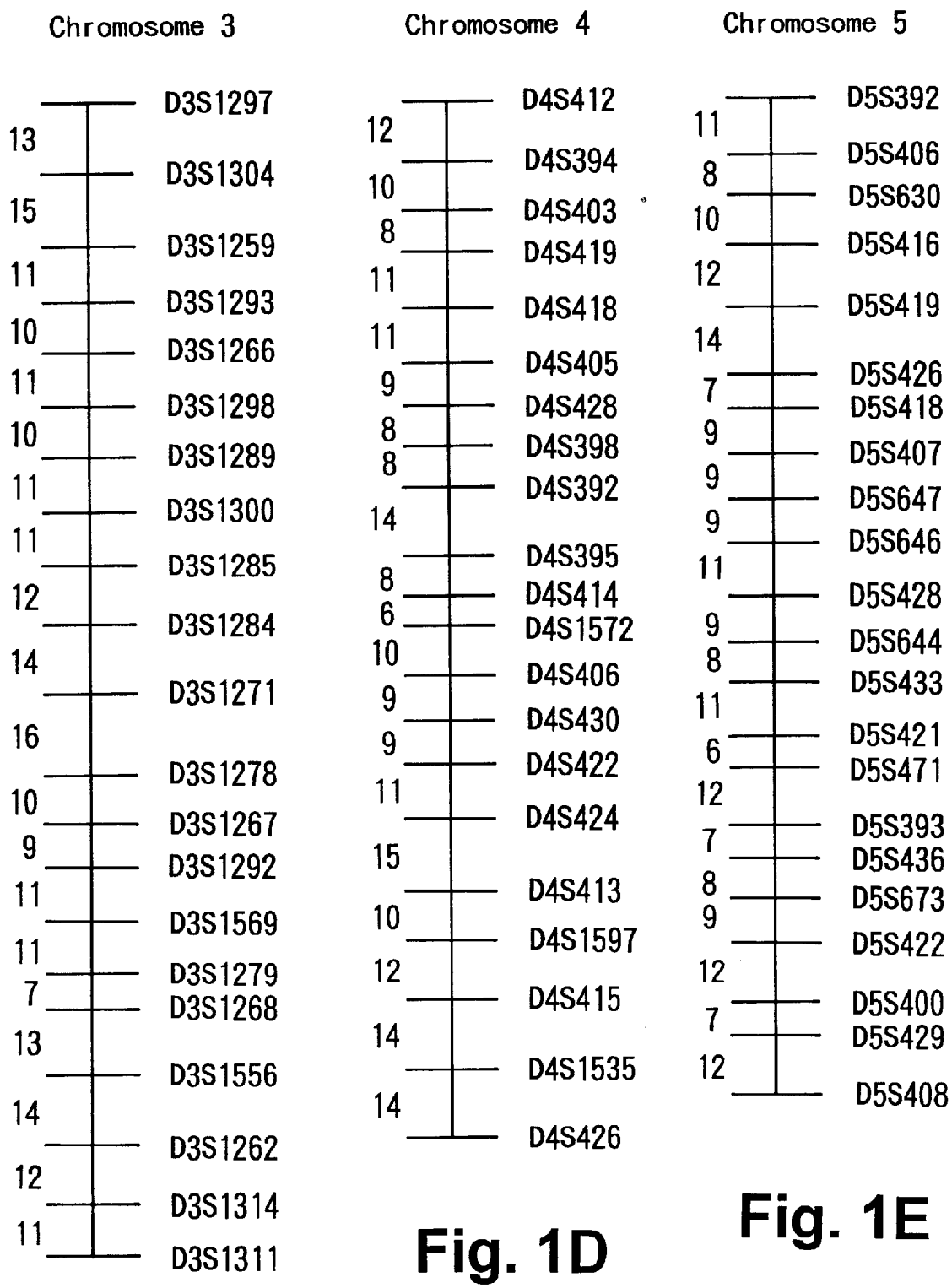

Using the extracted genomic DNA as template, microsatellite marker genes corresponding to the chromosomal loci shown in FIGS. 1 to 3 were amplified by PCR using fluorescently labeled primers (manufactured by Perkin-Elmer Co.). Herein, the marker D1S502 was not used because of the technical toughness for DNA amplification. For detailed analysis of the region HLA-D, individual genes of D6S299, D6S265 and D6S273 were amplified in place of D6D276. In addition to the amplification of the microsatellite DNAs, genes in the vicinity of the region HLA-DRB1 were also amplified by PCR using restriction fragment length polymorphism (RFLP) markers; in total, 359 marker sites were examined.

The composition of the PCR solution (15 μl) for microsatellite DNA amplification was as follows; DNA (30 ng), primers in mixture (0.2 μM), dNTP (each 0.2 mM), DNA polymerase (1 unit), $MgCl_2$ (2.5 mM) and 1×PCR buffer II. Amplification was conducted under the following conditions; denaturation at 94° C. for 10 minutes, denaturation (94° C. for 30 seconds), annealing at 55° C. for 1 minute and extension at 72° C. for 2 minutes, the program was repeated for 27 cycles, but the last extension was conducted at 72° C. for 5 minutes.

Figure 4:
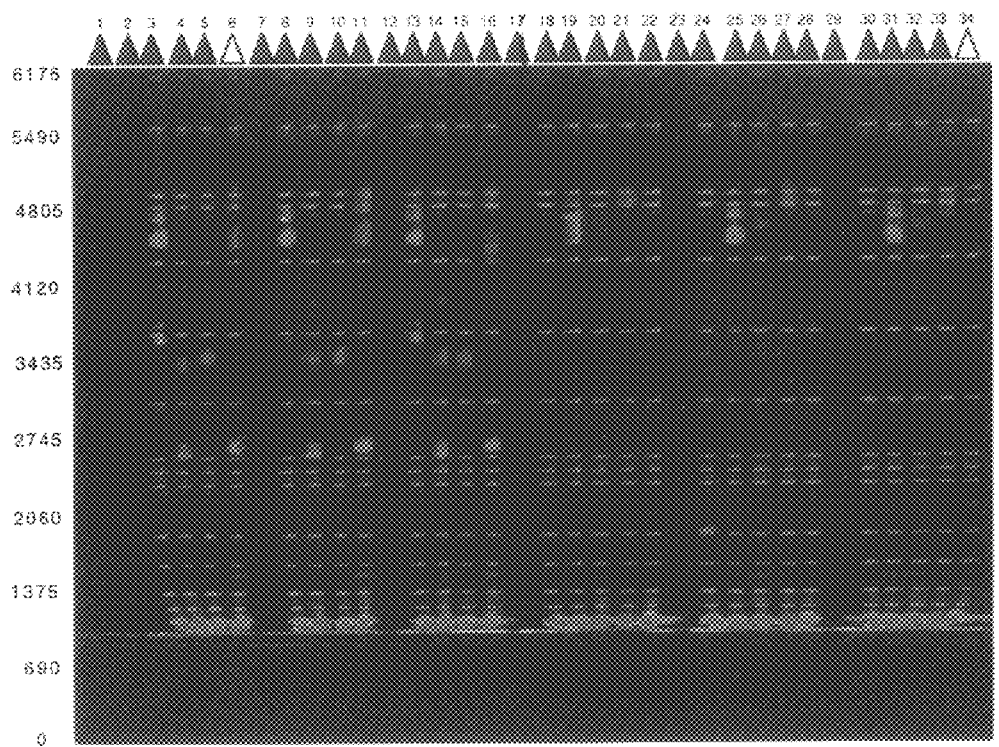
FIG. 4 shows one example of the gel electrophoresed PCR products.
Figure 5:
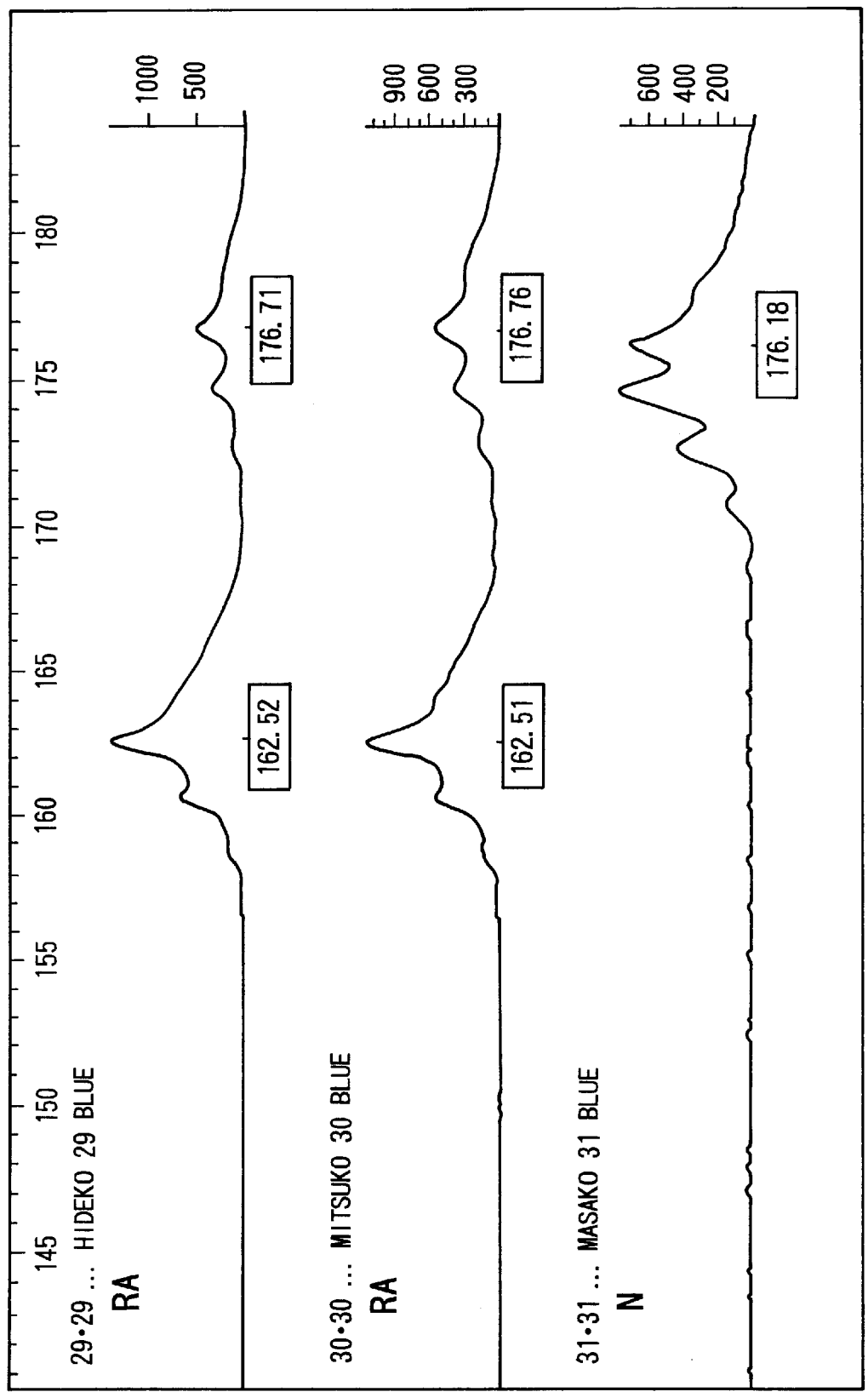
FIG. 5 shows one example of the Genotyper analysis of the PCR products.
Figure 6A:
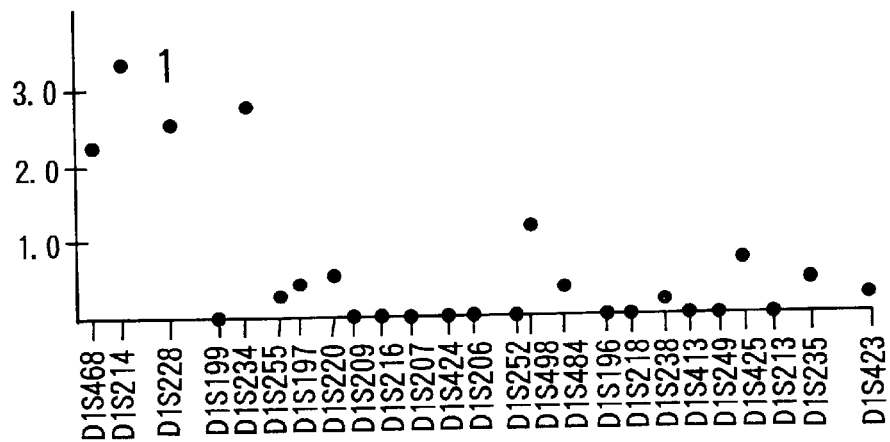
FIG. 6 depicts the results of the MLS values of the analyzed microsatellite markers, as plotted vs the chromosomes 1 to 6.
Figure 6B:
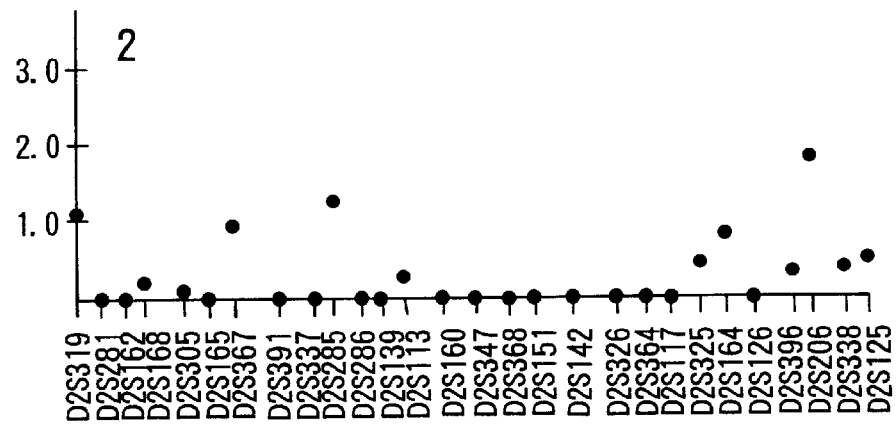
Figure 6C:
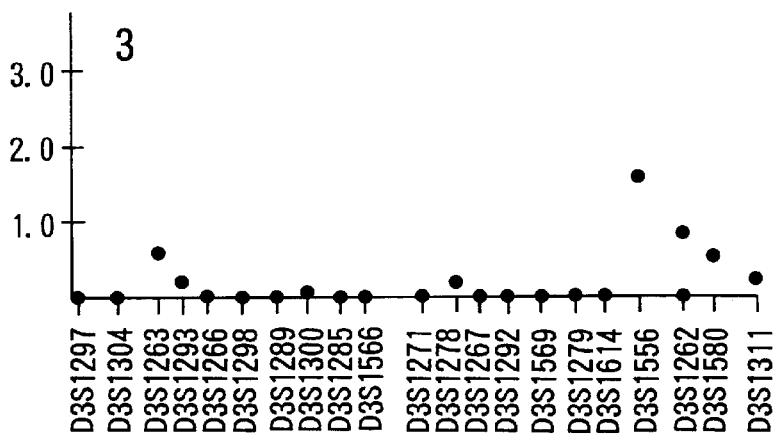
Figure 6D:
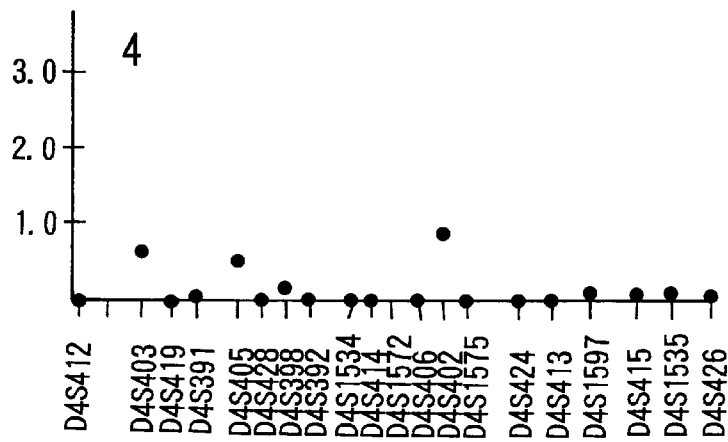
Figure 6E:
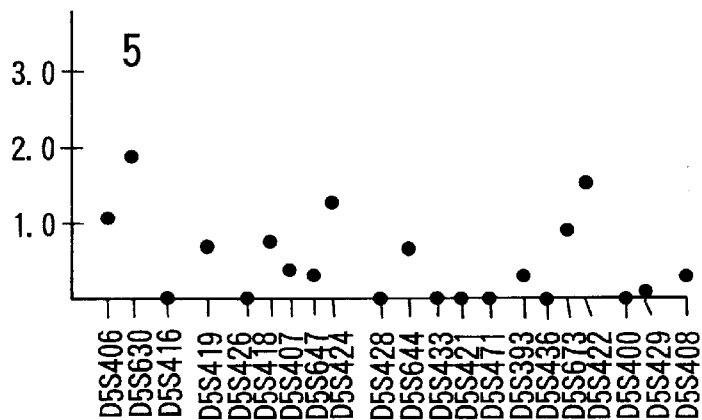
Figure 6F:
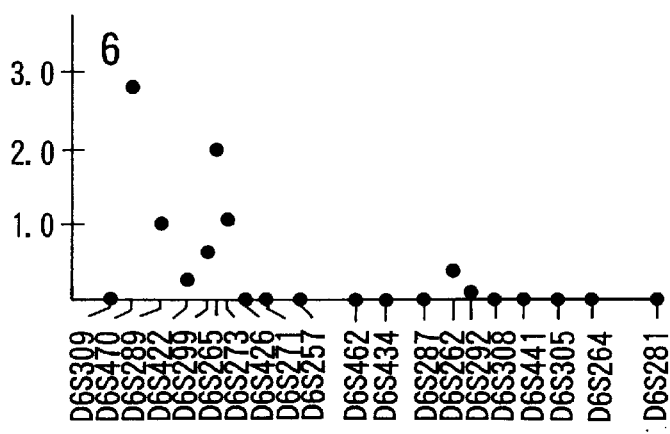
Figure 7A:
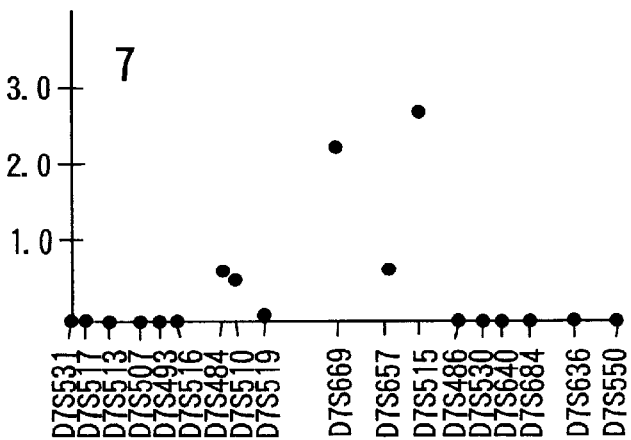
FIG. 7 depicts the results of the MLS values of the analyzed microsatellite markers, as plotted vs the chromosomes 7 to 12.
Figure 7B:
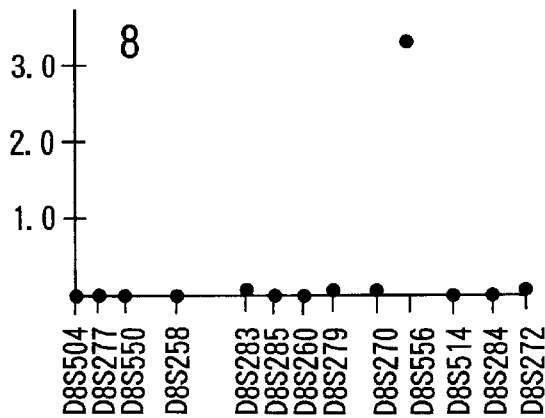
Figure 7C:
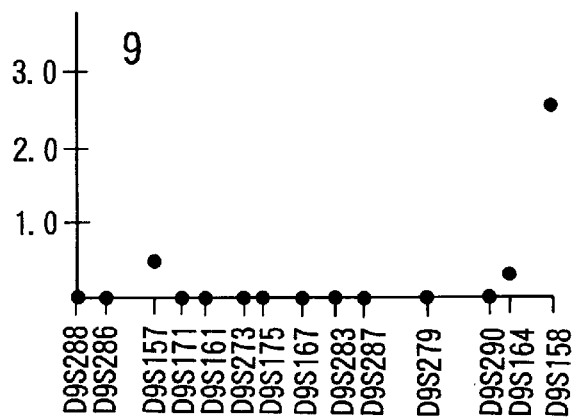
Figure 7D:
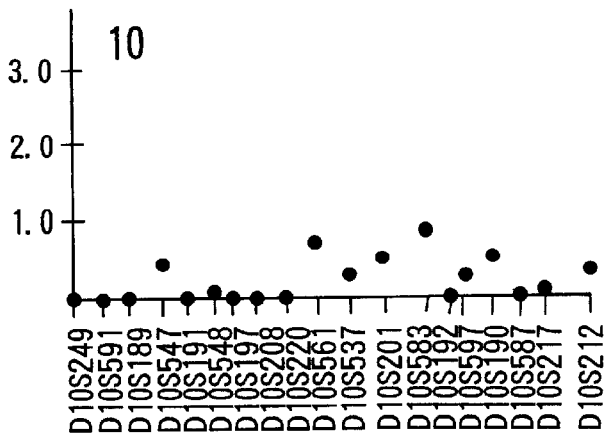
Figure 7E:
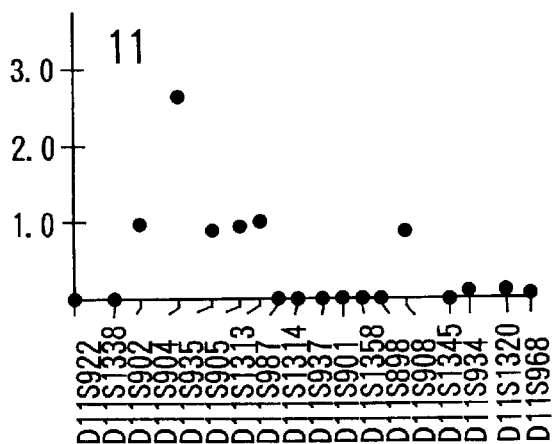
Figure 7F:
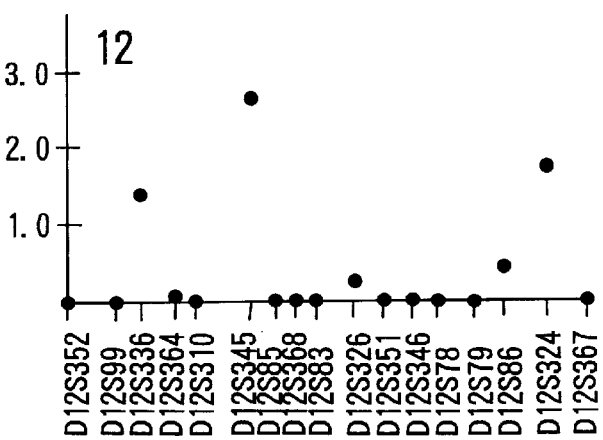
Figure 8A:
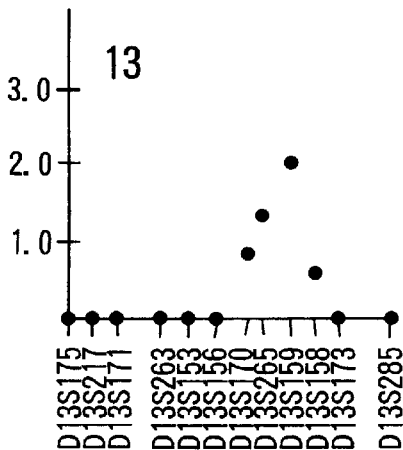
FIG. 8 depicts the results of the MLS values of the analyzed microsatellite markers, as plotted vs the chromosomes 13 to 18.
Figure 8B:
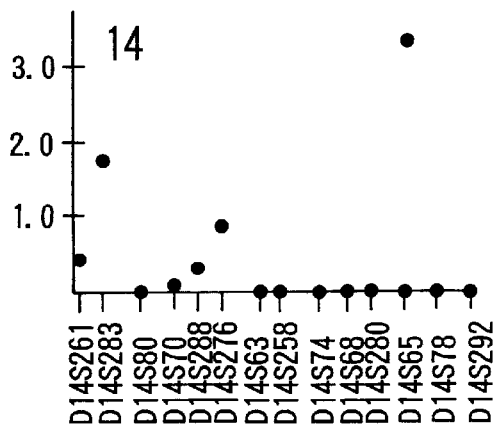
Figure 8C:
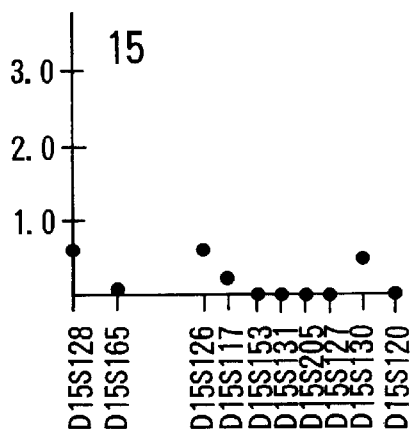
Figure 8D:
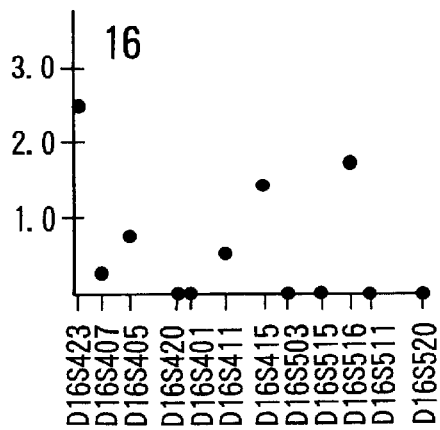
Figure 8E:
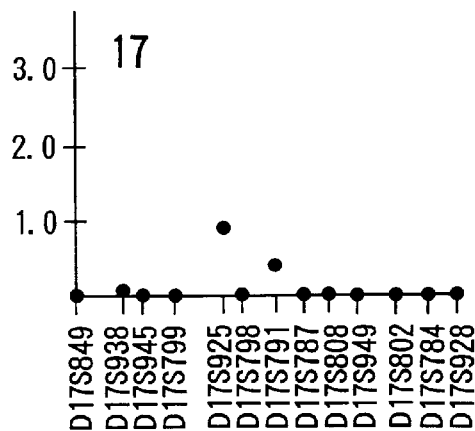
Figure 8F:
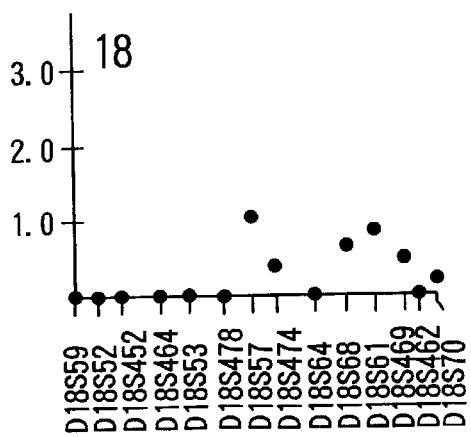
Figure 9A:
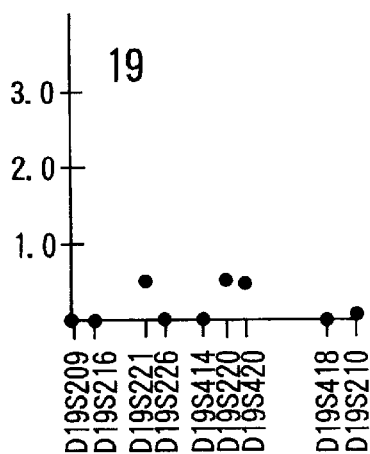
FIG. 9 depicts the results of the MLS values of the analyzed microsatellite markers, as plotted vs the chromosomes 19 to X.
Figure 9B:
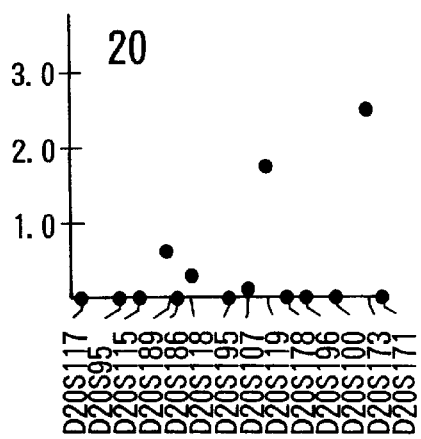
Figure 9C:
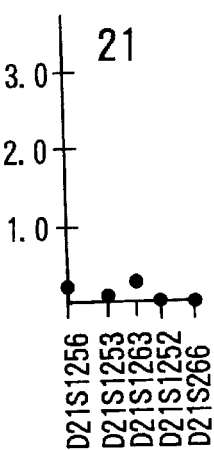
Figure 9D:
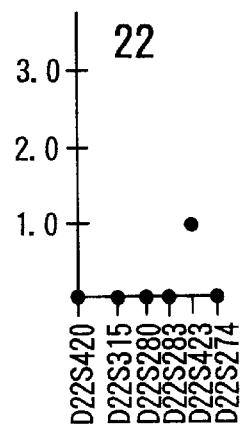
Figure 9E:
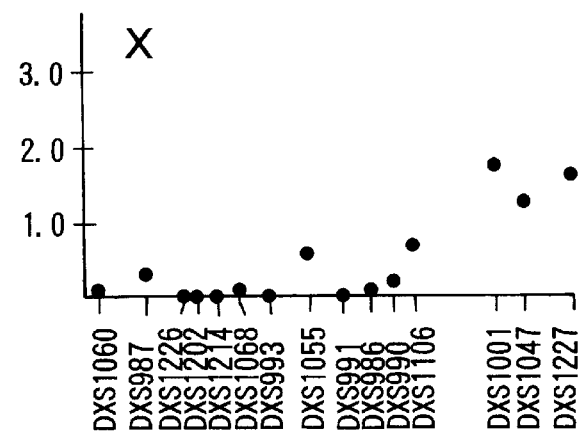

Individual PCR products labeled with 6-FAM, TET or HEX were electrophoresed, together with TAMURA-labeled size standards, on one gel panel (4% acrylamide/6 M urea) in a DNA sequencer (ABI 337: manufactured by Applied BioSystems, Co. Ltd.). FIG. 4 shows one example of the electrophoresis. According to the method, electrophoretic error could be reduced greatly, because the peaks, sizes and regions of DNA fragments were analyzed with reference to the size standards patterned. Subsequently, the individual marker genes were sized on the basis of the positions of the fluorescent images incorporated on a computer system, to determine how the genes derived from parents could be inherited per one pedigree. Furthermore, the electrophoretic results were subjected to gene scanning analysis and subsequent sizing with an analysis software Genotyper. FIG. 5 shows one example of the analysis results with Genotyper.

3. Linkage analysis

The sib-pair analysis method using linkage analysis by means of microsatellite marker has already been known in the identification of the causative gene of type I diabetes mellitus (Proc. Natl. Acad. Sci., 92: 8560–8565, 1995). However, the method cannot be applied as it is with no modification to subjects with rheumatoid arthritis. The reason is that general sub-pair analysis method determines the genetic mode of IBD (identical by descent) between a patient and both the parents thereof and that both the parents of individual patients with rheumatoid arthritis as one of senile diseases are dead in most of the cases at the onset of the disease so no definite IBD value can be determined in such cases In accordance with the invention, 35 families composed of Patient A, Patient B and a normal sibling member C were analyzed for IBD determination. More specifically, the IBD value is designated as 1 provided that both of the affected sibling members are endowed with the essential gene "a" of a parent; IBD=2 provided that the afflicted sibling members share individual alleles in common and that the individual alleles are imparted from either one of the parents. When both the parents are already dead with no possibility of typing of the genes of the parents, IBD cannot definitely be defined. Provided that the distribution of a certain arbitrary gene marker in a race population as a analysis subject is defined, the IBD value nevertheless can be determined by using the frequency of the allotype of the gene. Provided that the apparent IBD agreement between patient A, patient B and a normal sibling member C is defined as (IBD between A and B, IBD between A and C and IBD between B and C) and that a certain arbitrary gene as a target is defined as "a" while others are defined "â", all the possibilities are shown as 27 cases as in Table 1.

TABLE 1

Case 1: (aa, aa, aa), (aâ, aâ, aâ), (ââ, ââ, ââ)
Case 2: (aa, aa, aâ), (aâ, aa, aa)
Case 3: (aa, aâ, aa), (aâ, aa, aa), (aa, aâ, aâ), (aâ, aâ, aâ)
Case 4: (aa, aa, aâ), (aâ, aa, aa), (aa, aâ, aâ), (aâ, aâ, aa)
Case 5: (aa, aa, aa), (aâ, aa, aa), (aa, aâ, aâ), (aa, aa, aâ), (aâ, aâ, aâ), (aâ, aa, aa), (aâ, aâ, aâ), (aa, aa, aa)
Case 6: (aa, aâ, aâ), (aâ, aa, aa)
Case 7: (aa, aâ, aâ), (aâ, aa, aâ), (aâ, aâ, aa), (aâ, aâ, aa)

According to formula 1 of Holmans & Clayton (Am. J. Hum. Genet. 57: 1221–1232, 1995) provided that the allotype frequency of the gene "a" is defined as "Pa", the Lod value (L value) can be determined as follows.

$$L = \sum_{P \in P} Pr\begin{pmatrix} \text{parental} \\ \text{genotypes } P \end{pmatrix} \left[ \prod_{j=1}^{Nu} Pr(gi \mid P) \right] \times$$

$$\sum_{j=0}^{2} Pr\begin{pmatrix} \text{genotypes of} \\ \text{affected pair} \end{pmatrix} \begin{vmatrix} jIBD, \\ P \end{vmatrix} z_j$$

For example, the L values of three sets of Case 1 are calculated as L11, L12 and L13 by the following formulas 2, 3 and 4, respectively.

$$L_{11} = P_a^4 z_0 + \tfrac{1}{2} P_a^3 (1+P_a) z_1 + 1/4 P_a^2 (1+P_a)^2 z_2 \qquad \text{Formula 2}$$

$$L_{12} = P_{\bar{a}}^4 z_0 + \tfrac{1}{2} P_{\bar{a}}^3 (1+P_{\bar{a}}) z_1 + 1/4 P_{\bar{a}}^2 (1+P_{\bar{a}})^2 z_2 \qquad \text{Formula 3}$$

$$L_{13} = 3 P_z^2 P_{\bar{a}}^2 z_0 + \tfrac{1}{2} P_a P_{\bar{a}} (1+2 P_a P_{\bar{a}}) z_1 + P_a P_{\bar{a}} (1+\tfrac{1}{2} P_a P_{\bar{a}}) z_2 \qquad \text{Formula 4}$$

In the same manner, the L values from L11 to L72 can be calculated. By the same calculation on all subjects, the L value of the gene "a" in a population can be calculated according to the formula 5.

$$L = \frac{n!}{n_{11}! n_{12}! \ldots n_{72}!} L_{11}^{n11} L_{12}^{n12} \ldots L_{72}^{n72} \qquad \text{Formula 5}$$

By subsequently permitting the variables $Z_0$, $Z_1$ and $Z_2$ to vary throughout the ranges under provisions of $Z_0 \leq \tfrac{1}{2}$, $Z_0 \leq \tfrac{1}{2} Z_1$, and $Z_0 + Z_1 + Z_2 = 1$, the maximum ($L_{max}$) of the L values can be determined. Under the provision of no emergence of any relationship between these markers and the actual gene, alternatively, the L value ($L_{null}$) can be calculated according to the formula 6, provided that $Z_0 = 0.25$, $Z_1 = 0.50$ and $Z_2 = 0.25$.

$$L_{null} = \frac{n!}{n_{11}! n_{12}! \ldots n_{72}!} L_{11}^{n11} L_{12}^{n12} \ldots L_{72}^{n72} \qquad \text{Formula 6}$$

Finally, the maximum Lod value (Maximum Lod Score:MLS) can be calculated according to the formula 7.

$$MLS = \log(L_{max}/L_{null})$$

FIGS. 6 to 9 depict the results of the MLS values of all the microsatellite markers of 359 in total as plotted vs each chromosome. First, herein, marker sites with MLS values around 3.0 are supposed to significantly correspond to the causative genes as well. In other words, the MLS value indicates the probability of the emergence of the relationship between one of the markers and one of the causative genes compared with the accidental emergence thereof and is represented in a logarithmic figure based on $\log_{10}$: at MLS= 3.0, the relationship is supposed to be present at a probability 1000-fold the probability of the accidental emergence thereof. More specifically, it is indicated that the microsatellite markers D1S214, D1S253, D8S556 and DXS1232 at extremely large MLS values around 3.0 are present very closely to the causative genes.

Figure 10A:
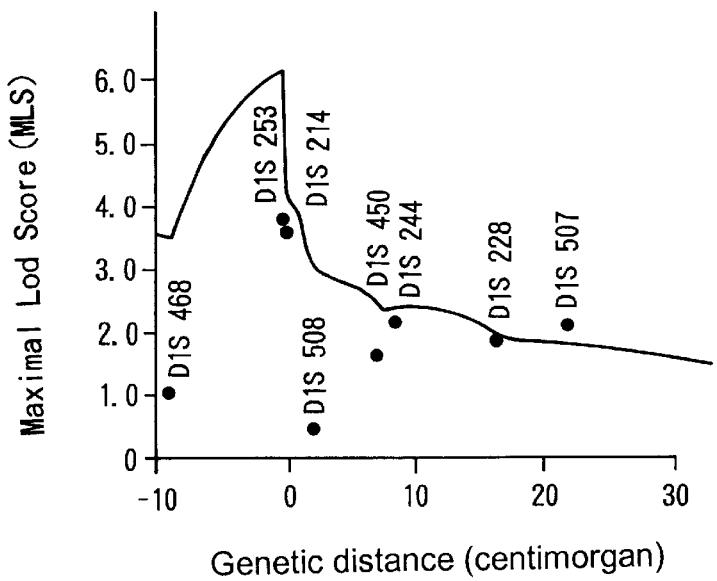
FIG. 10 graphically shows the relationship between the MLS values of the individual microsatellite markers at multiple marker sites including the marker sites indicating the inventive disease genes and the distances (in unit centimorgan) thereof from the target disease genes on the chromosome 1 (upper panel), the chromosome 8 (middle panel) and the X chromosome (lower panel).
Figure 10B:
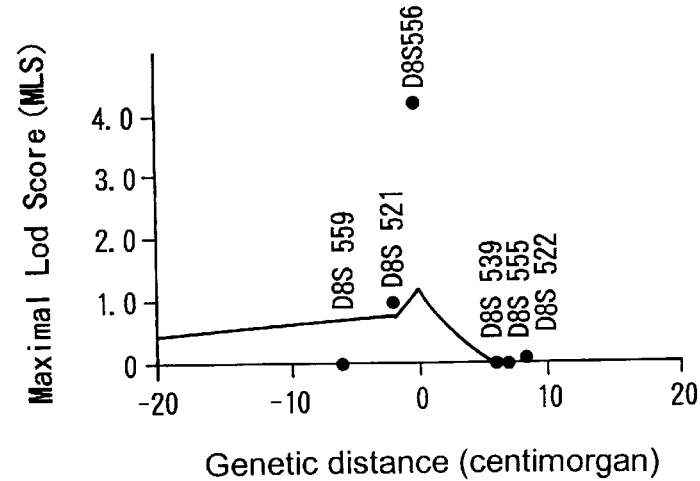
Figure 10C:
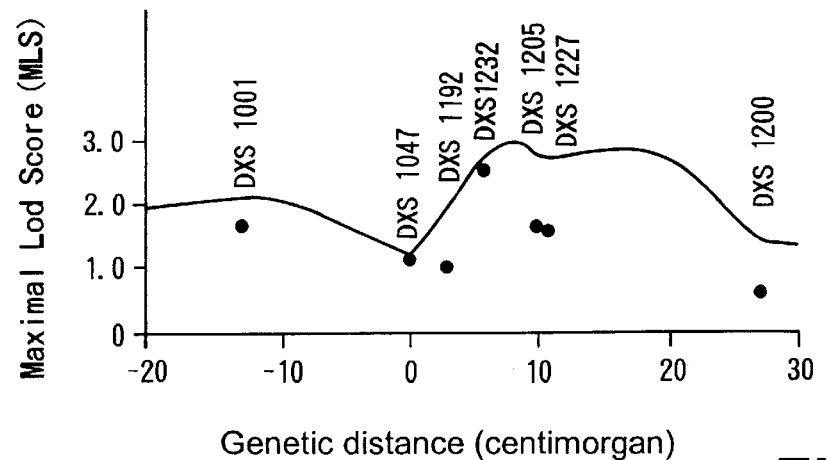

FIG. 10 graphically shows the relationship between the MLS values of the individual microsatellite markers at multiple marker sites including the four marker sites and the distances (in centimorgan) thereof from the disease genes on the chromosome 1 (upper panel), the chromosome 8 (middle panel) and the X chromosome (lower panel). As shown in FIG. 10 a target disease gene of rheumatoid arthritis is present at a position very close to the sites of the microsatellite markers D1S214 and/or D1S253 on human chromosome 1. Similarly, the disease genes are present at a position very close to the site marked with the microsatellite marker D8S556 on human chromosome 8 and at a position very close to the sites marked with microsatellite markers DXS1001, DXS1047, DXS1205, DXS1227 and/or DXS1232 on human X chromosome.

The disease genes of rheumatoid arthritis in accordance with the invention are present at such specific chromosomal loci as described above (genes present at least at one or more of positions within ±1 centimorgan from the 8 sites marked with the microsatellite markers); once the coding regions and DNA sequences thereof are identified and determined by known methods such as positional cloning, the disease genes can make profound contributions to the establishment of an effective therapeutic method thereof. The PCR amplification and analysis of the microsatellite genes used in accordance with the invention are applicable to the diagnosis of rheumatoid arthritis and the identification of the causative factors thereof. More specifically, by amplifying the genome DNA of a patient with the potential onset of the disease by PCR using the markers corresponding to the chromosomal sites as primers and comparing the resulting amplified products with the genome DNA of a normal control by the analysis the Genotyper as shown in FIG. 5, the potential subsequent onset of the disease can be estimated at a high precision.

INDUSTRIAL APPLICABILITY

The invention provides the disease genes of human rheumatoid arthritis, a method for diagnosing rheumatoid arthritis using the mutations of these disease genes as the indicators, and a method for determining the causative factors thereof. These aspects of the invention are applicable to the development of pharmaceutical medicines and therapeutic strategies.

What is claimed is:

1. A method for determining the susceptibility of a patient to rheumatoid arthritis, comprising:

a) obtaining a sample containing genetic material from said patient;

b) amplifying the genomic DNA of said patient and a normal control patient wherein the genomic DNA amplified is selected from the group consisting of the microsatellite markers D1S214, D1S253, and D8S556;

c) comparing the size of the amplification products from said patient to control; and d) identifying the patient whose amplification products are a different length from those of normal control as a patient susceptible to rheumatoid arthritis.

* * * * *